United States Patent [19]

Grier et al.

[11] 4,244,963
[45] Jan. 13, 1981

[54] 1-[2-(ALKYL AND ARYLSULFONYL)-2-PROPENYL AND PROPYL] SUBSTITUTED PIPERIDINES USEFUL AS ANTIMICROBIAL AND ANTIINFLAMMATORY AGENTS

[75] Inventors: Nathaniel Grier, Englewood; Richard A. Dybas, Somerville; Bruce E. Witzel, Rahway, all of N.J.

[73] Assignee: Merck & Co., Inc., Rahway, N.J.

[21] Appl. No.: 79,281

[22] Filed: Sep. 27, 1979

[51] Int. Cl.³ ............... C07D 211/46; A61K 31/445
[52] U.S. Cl. .............................. 424/267; 424/263; 546/186; 546/187; 546/189; 546/190; 546/191; 546/193; 546/194; 546/208; 546/209; 546/210; 546/212; 546/213; 546/214; 546/216; 546/221; 546/222; 546/223; 546/225; 546/232; 546/233; 546/235; 546/236; 546/237; 546/238; 546/239; 546/240; 546/242; 546/244; 546/246; 546/247; 546/248
[58] Field of Search ............... 546/186, 187, 188, 189, 546/190, 191, 193, 194, 208, 209, 210, 212, 213, 214, 216, 221, 242, 248, 223, 222, 225, 236, 237, 238, 239, 240, 244, 245, 246, 247, 232, 233, 234, 235; 424/267, 263

[56] References Cited
U.S. PATENT DOCUMENTS

| | | | |
|---|---|---|---|
| 3,487,469 | 12/1969 | Marxer | 546/240 |
| 4,145,426 | 3/1979 | Grier et al. | 546/187 |

OTHER PUBLICATIONS

Dybas et al., "Developments in Industrial Microbiology" vol. 19, pp. 347–353 (1978).

*Primary Examiner*—Henry R. Jiles
*Assistant Examiner*—Robert T. Bond
*Attorney, Agent, or Firm*—Raymond M. Speer; Mario A. Monaco

[57] ABSTRACT

1-[2-(Alkyl and arylsulfonyl)-2-propenyl and propyl] substituted piperidines of the formula:

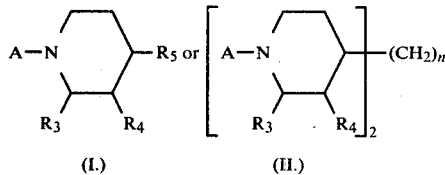

where A is

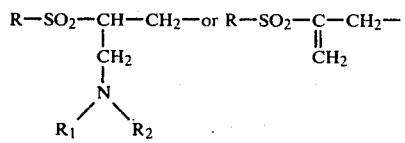

and $R_1$–$R_5$ are various substituents, are useful as antimicrobial and anti-inflammatory agents.

18 Claims, No Drawings

1-[2-(ALKYL AND ARYLSULFONYL)-2-PROPENYL AND PROPYL] SUBSTITUTED PIPERIDINES USEFUL AS ANTIMICROBIAL AND ANTIINFLAMMATORY AGENTS

BACKGROUND OF THE INVENTION

1. Field of the Invention

The present invention is concerned with novel 1-[2-(alkyl and arylsulfonyl)-2-propenyl and propyl] substituted piperidine compounds; with antimicrobial compositions and their use in protecting industrial products and systems of a wide variety against the deteriorating action of bacteria and fungi; and with anti-inflammatory compositions and their use in treating pain, fever and inflammation.

2. Brief Description of the Prior Art:

The compound 1-[2-(methylsulfonyl)-2-propenyl]-4-piperidinol is disclosed in Dybas et al., *Developments in Industrial Microbiology*, Vol. 19, pp. 347-353 (1978). However, the compounds of the present invention are not the same as the compound of the prior art, and, moreover, the prior art compound possesses no effective, stable antimicrobial activity, as is shown by the disclosure of the cited reference.

SUMMARY OF THE INVENTION

In accordance with the present invention, there is provided novel compounds of the formula:

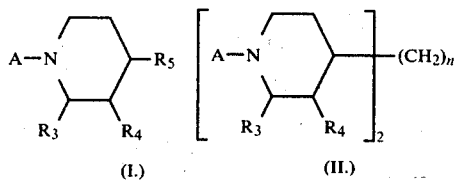

wherein
A is

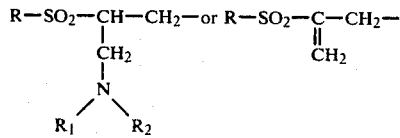

R is selected from the group consisting of $C_{3-18}$ alkyl, straight or branched chain, for example propyl or tert-butyl; $C_{2-8}$ alkenyl, for example propenyl or pentenyl; $C_{3-7}$ cycloalkyl for example cyclopropyl; aryl, for example phenyl, naphthyl, tolyl, or xylyl; aryl substituted with a member selected from the group consisting of halogen, $C_{1-4}$ alkyl, $C_{1-4}$ alkoxy, $C_{1-4}$ alkoxy $C_{1-4}$ alkyl, and nitro; aralkyl, for example benzyl or phenethyl; aralkyl substituted with a member selected from the group consisting of halogen, $C_{1-4}$ alkyl, $C_{1-4}$ alkoxy, $C_{1-4}$ alkoxy $C_{1-4}$ alkyl, and nitro; and a heterocycle selected from the group consisting of imidazoyl, thienyl, thiazolyl, pyridyl; furyl; and tetrahydrofuran-2-yl;

$R_1$ and $R_2$ are independently selected from the group consisting of hydrogen; $C_{1-18}$ alkyl, for example ethyl or propyl; $C_{2-8}$ alkenyl, for example ethenyl or butenyl; hydroxy $C_{1-8}$ alkyl, for example hydroxymethyl; and cyclo $C_{4-8}$ alkyl, for example cyclopropyl; or $R_1$ and $R_2$ taken together with the nitrogen atom form a five- or six- membered saturated heterocyclic ring substituted at the 2-, 3-, and 4- position with $R_3$, $R_4$, and $R_5$, respectively;

$R_3$, $R_4$, and $R_5$ are selected from the group consisting of hydrogen; $C_{1-3}$ alkyl, for example methyl; $C_{2-3}$ alkenyl, for example propenyl; halogen, for example chloro and fluoro; hydroxy; hydroxy $C_{1-3}$ alkyl, for example hydroxyethyl; phenyl; carboxyl; carboxamido; $C_{1-4}$ alkyl N- mono- and N,N-disubstitutedcarbonylamino, for example N,N-dimethylcarbonylamino; $C_{1-4}$ alkoxycarbonyl, for example ethoxycarbonyl; 1-pyrrolidinyl; and 1-piperidinyl; and n is 0 to 3;

and acid addition and quaternary salts thereof.

Examples of preferred novel compounds of the present invention are:

1-[2-(n-propylsulfonyl)-2-propenyl]-4-piperidinol
1-[2-(phenylsulfonyl)-2-propenyl]-4-piperidinol
2-(n-propylsulfonyl)-1,3-propanediylbis(4-hydroxypiperidine)

Both Formula I and Formula II compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The present invention also provides antimicrobial compositions for use in protecting industrial products and systems of a wide variety against the deteriorating action of bacteria and fungi. The novel compounds of the present invention are the active ingredients in antimicrobial compositions used, for example, as preservatives for aqueous systems such as latex paints. The novel compounds of the present invention are effective against gram positive and gram negative bacteria as well as fungi in such diverse systems as cooling tower water systems, paper mill white water, in brines for enhanced oil recovery, in cutting oil emulsions, resin emulsions, aqueous adhesives, and the like. Concentrations of from 0.001% up to 0.5% may be employed, depending upon the system and degree of microbial contamination. The antimicrobial compositions of the present invention may be added as neat active ingredient in the form of a powder or liquid, in solution or as dispersions and emulsions in aqueous or non-aqueous media, or admixed with inert solid carriers. Adjuvants such as surfactants, spreading agents, defoamers, other antimicrobials, dyes, antifreeze ingredients, film coalescents, and the like may be used.

In accordance with the present invention there is further provided anti-inflammatory compositions for use in treating pain, fever, and inflammation. The novel compounds of the present invention possess a high degree of anti-inflammatory, analgesic and anti-pyretic activity. They are of value in the treatment of arthritic and dermatological disorders or like conditions responsive to anti-inflammatory drugs. In general they are indicated for a wide variety of conditions where one or more of the symptoms of inflammation, fever and pain are manifested. Included within this category are diseases such as rheumatoid arthritis, osteo arthritis, gout, infectious arthritis and rheumatic fever. As indicated above the compounds utilized in the practice of the invention also possess a useful degree of analgesic and anti-pyretic activity.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are sutable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl-cellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial eters derived from fatty acid anhydrides and hexitol, for example polyoxyethylene sorbitan monooleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspension may contain a thickening agent, for example beeswax, hard paraffin or cetyl alcohol. Sweetening agents, such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acid anhydrides and hexitol, for example sorbitan mono-oleate, and condensation products of the said partial esters with ethylene oxide, for example polyoxyethylene sorbitan mono-oleate. The emulsions may also contain sweetening and flavouring agents.

Syrups and elixirs may be formulated with sweetening agents, for example glycerol, sorbitol or sucrose. Such formulations may also contain a demulcent, a preservative and flavouring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

For topical use, creams, ointments, jellies, solutions or suspensions, etc. containing the anti-inflammatory agents are employed.

Dosage levels of the order of 20 mg. to 1 gram per day are useful in the treatment of the above indicated conditions. For example, inflammation is effectively treated and anti-pyretic and analgesic activity manifested by the administration of from about 0.3 to 60 milligrams of the compound per kilogram of body weight per day. Advantageously from about 2 mg. to about 30 mg. per kilogram of body weight and especially from about 4 mg. to about 20 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of Formula I wherein A is

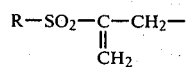

may be prepared by techniques involving the condensation of 2-, 3-, and/or 4- substituted piperidines, formaldehyde, and various sulfonylacetic acids, as illustrated in the following reaction scheme:

A.
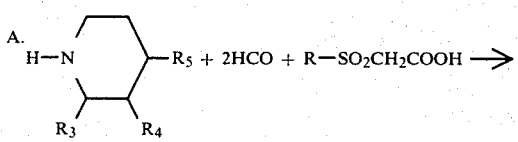

-continued

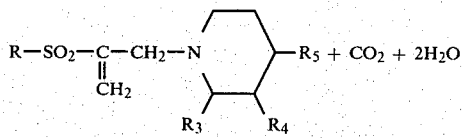

The compounds of Formula I wherein A is

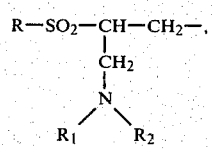

which are shown in the following formula:

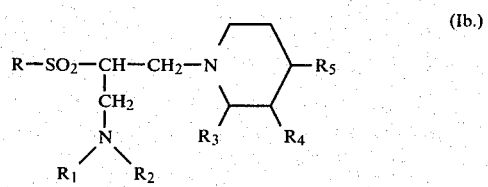

(Ib.)

may be prepared by several methods. A mole of amine of the formula:

(III.)

may be added to the olefin of Formula Ia., as illustrated in the following reaction scheme:

B.
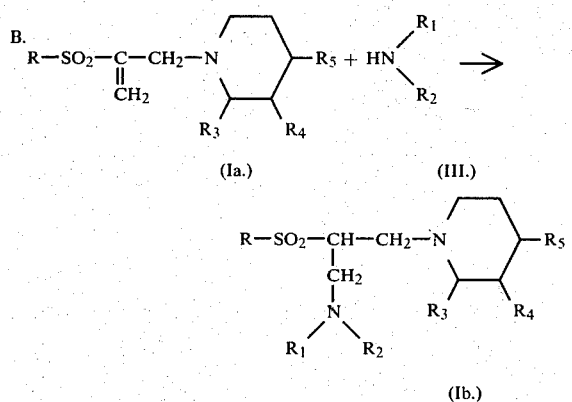

Alternatively, the secondary amine of Formula III. may be employed initially to prepare the olefinic Mannich derivative of the following formula:

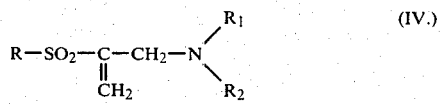

(IV.)

to which is then added one mole of a substituted piperidine of the formula

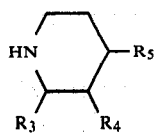 (V.)

in order to form compounds of Formula Ib. in accordance with the following reaction scheme:

C.

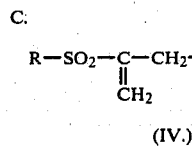 (IV.) + 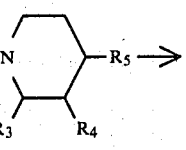 (V.) →

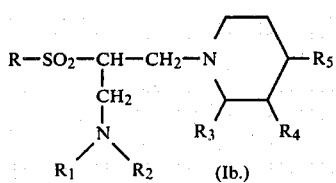 (Ib.)

It is also possible to modify procedure A. above by increasing the molar ratio of amine:formaldehyde:sulfonylacetic acid from 1:2:1 to 2:2:1 in order to provide compounds of Formula Ib. having the following structure:

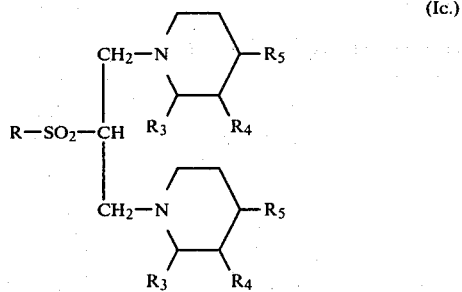 (Ic.)

One mole of amine may then be eliminated from the compound of Formula Ic., as for example with heat, salt formation with oxalic acid, or steam distillation, to form compounds of Formula Ia., as is illustrated in the following reaction scheme:

D. 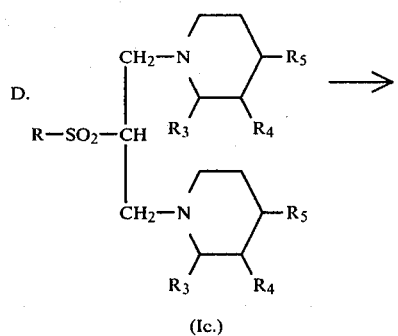 →

(Ic.)

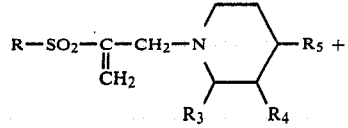 +

(Ia.)

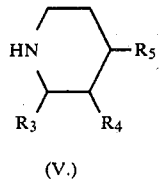

(V.)

Still other methods may be employed, but the preferred procedure is that illustrated in A. above, followed by amine addition. The compounds of Formula Ib. which contain identical substituted piperidine groups are readily prepared by this route.

A variety of solvents may be used for the reaction of procedure A. including water, alcohols, ethers as well as an excess of one of the reagents other than acetone. The amines can be used in procedure A. as free bases or in form of salts such as the acetate or hydrochloride. Generally, elevated temperatures are required in the range of 45° C. to 110° C. and reaction periods of from 1 to 24 hours. Isolation of products may be accomplished by crystallization or distillation. Any other chemical groupings present in the organic bases employed for procedure A. which contain active hydrogen should preferably be blocked and afterwards liberated by techniques well known in the art.

The addition reactions of Formula Ia. olefinic compounds with amines to provide Formula Ib. derivatives may be run with a 1:1 molar ratio of reactants in solvents such as water, alcohols, dioxane or mixtures of these or neat. Generally, no heat is required and reaction times may range from ½ to 10 hours. The course of the reaction is readily monitored by measuring the disappearance of the alpha beta unsaturated ketonic moiety as with ultraviolet or infra-red spectral analysis.

The compounds of Formula II. may be prepared in accordance with the procedures described above for preparing the compounds of Formulas Ia. and Ib., substituting for the piperidines employed therein, the appropriate dipiperidine compound.

The intermediates required in the synthesis of the compounds of the present invention, namely piperidine and its substitution products, and alkyl-, aryl-, aralkyl, and heteroarylsulfonylacetic acids are well-known or readily prepared by known methods. The piperidine derivatives are described in our U.S. Pat. No. 4,145,426, and methods of preparation of the various sulfonylacetic acids are typified by the description in Balasubramanian et al., *J. Chem. Soc.*, 3296 (1955) for alkylsulonylacetic acids. The well-known alkylthioacetic acids are oxidized at room temperature with dilute potassium permanganate in acetone to the sulfonylacetic acids. Improved yields may be obtained by conducting the oxidation at neutral pH in water according to the method of Carpenter and Shaw, *J. Chem. Soc.*, 2016 (1970). The arylthioacetic acids are treated similarly. They are readily available from the reaction of substituted benzenethiols with chloroacetic acid under mildly alkaline conditions following the procedure of Noble and Thompson, *J. Pharm. Sci.,* 54, 576 (1965).

The following examples illustrate preparation of the intermediates in accordance with the procedures described above.

p-Chlorophenylthioacetic Acid 72.0 g. (0.76 mole) of α-chloroacetic acid, 40.0 g. of sodium bicarbonate, and 2 l. of water were placed in a 4 l. beaker and 110 g. (0.76 mole) of p-chlorobenzenethiol and 30 g. of sodium hydroxide in 200 ml. of water were added. After 0.5 to 2 hrs. on a steam bath the mixture was cooled, filtered, and the filtrate treated with 41 ml. of sulfuric acid (previously diluted to 100 ml. with water). The product was collected on a Büchner funnel and purified by dissolving in dilute aqueous sodium hydroxide, then treated with activated charcoal, filtered, and acidified. There was obtained in this manner, 78.5% yield of the final product, m.p. 105.5°–106° C.

p-Chlorobenzenesulfonylacetic Acid

Oxidation of the p-chlorophenylthioacetic acid obtained as described above, by the procedure of Backlund, *Chem. Abstr.,* 34, 7860 (1940), which also employed potassium permanganate in water at room temperature, gave a 76.8% yield of the sulfonylacetic acid, m.p. 125°–127° C.

The following examples will serve to illustrate preparation of the novel compounds of the present invention.

EXAMPLE 1

1-[2-(Propylsulfonyl)-2-propenyl]-4-piperidinol

In a 1 l. 3-neck round bottom flask, under a nitrogen atmosphere, 13 g. (0.078 mole) of n-propylsulfonylacetic acid was dissolved in 75 ml. of dioxane. There was then added with good stirring a solution of 7.89 g. (0.078 mole) of 4-hydroxypiperidine in 75 ml. of dioxane and 5 ml. of water (obtained by warming to 40° C.). The almost clear solution was kept at 30° C. and over a 10 minute period 12.7 g. of a 37% aqueous formaldehyde solution (0.156 mole) was dripped in. After complete addition there was gradual warming of the reaction mixture to 50° C. with carbon dioxide evolution. The temperature rose to 57° C. with vigorous gas evolution; and the reaction mixture was maintained at 57° C. for 4 hours, followed by stirring for 12 hours at 20°–25° C. The solvents were removed in vacuo; the residual oil was taken up in methylene chloride, washed well with water, dried over anhydrous sodium sulfate, again concentrated, then taken up in ether (120 m.), washed twice with 10 ml. of water, dried over anhydrous sodium sulfate; and the solvent was removed to leave 7 g. of the product as an oil.

Following the procedures of Example 1, and substituting for the n-propylsulfonylacetic acid and 4-hydroxypiperidine, equimolar amounts of other sulfonylacetic acids and substituted piperidines, there may be prepared additional novel compounds of the present invention, as shown in the following table:

| Substituted Sulfonyl-acetic Acid | Substituted Piperidine | Product |
|---|---|---|
| t-butyl | 3,4-dichloro | 1-[2-(t-butylsulfonyl)-2-propenyl]3,4-dichloro-piperidine |
| n-hexyl | 2-methyl-4-hydroxy | 1-[2-(n-hexylsulfonyl)-2-propenyl]-2-methyl-4-piperidinol |
| 2-ethylhexyl | 3-hydroxymethyl | 1-[2-(2-ethylhexylsulfonyl)-2-propenyl]-3-hydroxymethylpiperidine |
| phenylmethyl | 4-carboethoxy | 1-[2-(phenylmethylsulfonyl)-2-propenyl]-4-carboethoxypiperidine |
| phenethyl | 3-N-methylcarboxamido | 1-[2-(phenethylsulfonyl)-2-propenyl]-3-N-methylcarboxamidopiperidine |
| n-decyl | 4-fluoro | 1-[2-(n-decylsulfonyl)-2-propenyl] 4-fluoro-piperidine |
| n-dodecyl | 4-carboxy | 1-[2-(n-dodecylsulfonyl)-2-propenyl] 4-carboxy-piperidine |
| n-tetradecyl | 2-methyl-4-phenyl | 1-[2-(n-tetradecylsulfonyl)-2-propenyl]-2-methyl-4-phenylpiperidine |
| n-butyl | 4-hydroxy-4-phenyl | 1-[2-(n-butylsulfonyl)-2-propenyl]-4-phenyl-4-piperidinol |
| t-butyl | 4,4'-bis(1,3-trimethylene) | 1,1'-[2-(t-butylsulfonyl)-2-propenyl]-4,4'-bis(1,3-trimethylene) dipiperidine |

EXAMPLE 2

1-[2-(Phenylsulfonyl)-2-propenyl]-4-piperidinol 4.0 g. (0.02 mole) of phenylsulfonylacetic acid was dissolved in 15 ml. of dioxane followed by a solution of 2.0 g. (0.02 mole) of 4-hydroxypiperidine in 20 ml. of dioxane and 2 ml. of water. At 30° C. 3.5 g. (0.04 mole) of 37% aqueous formaldehyde was added rapidly and the reaction mixture agitated thoroughly. The temperature was gradually raised by means of an oil bath to 42° C. and carbon dioxide evolution was initiated. The mixture was maintained at approximately 42° C. for an additional 2 hours. The solvent was removed under reduced pressure and the product was obtained as a residue.

Following the procedures of Example 2, and substituting for the phenylsulfonylacetic acid and 4-hydroxypiperidine, equimolar amounts of other sulfonylacetic acids and substituted piperidines, there may be prepared additional novel compounds of the present invention, as shown in the following table:

| Substitited Sulfonyl-Acetic Acid | Substituted Piperidine | Product |
|---|---|---|
| phenyl | 3,4-di(hydroxymethyl) | 1-[2-(phenylsulfonyl)-2-propenyl]-3,4-di(hydroxymethyl)piperidine |
| 4-chlorophenyl | 4-carbomethoxy | 1-[2-(4-chlorophenylsulfonyl)-2-propenyl]-4-carbomethoxypiperidine |
| 2-naphthyl | 3-carboxy | 1-[2-(2-naphthylsulfonyl)-2-propenyl]-3-carboxy-piperidine |
| 2-methoxyphenyl | 4-chloro | 1-[2-(2-methoxyphenylsulfonyl)-2-propenyl]-4-chloropiperidine |
| 3-pyridyl | 2-methyl | 1-[2-(3-pyridylsulfonyl)-2-propenyl]-2-methyl-piperidine |
| 2-furyl | 2,3,4-trimethyl | 1-[2-(2-furylsulfonyl)- |

| | | -continued |
|---|---|---|
| 2-thienyl | 3-N-butylcarbox-amido | 2-propenyl]-2,3,4-tri-methylpiperidine<br>1-[2-(2-thienylsulfonyl)-2-propenyl]-3-N-butyl-carboxamidopiperidine |
| 4-thiazolyl | 4-carboxamido | 1-[2-(4-thiazolylsulfonyl)-2-propenyl]-4-carbox-amidopiperidine |
| 5-methoxymeth-yl-2-furyl | 4-hydroxy | 1-[2-(5-methoxymethyl-2-furyl)-2-propenyl] 4-piperidinol |
| 2-nitrophenyl | 2-methyl-5-ethyl | 1-[2-(2-nitrophenylsul-fonyl)-2-propenyl]-2-methyl-5-ethylpiperidine |

EXAMPLE 3

2-(n-Propylsulfonyl)-1,3-propanediylbis(4-hydroxypiperidine)

1-[2-(n-Propylsulfonyl)-2-propenyl]-4-piperidinol, 2.5 g. (0.01 mole) is dissolved in 30 ml. of dioxane and mixed with a solution of 1.0 g. (0.01 mole) of 4-hydroxypiperidine in 10 ml. of dioxane and 1 ml. of water. The reaction mixture is allowed to stand at 15°–20° C. for 12 hours. Completion of the addition reaction is determined using thin layer chromatography on silica gel with benzene-methyl alcohol development. The appearance of a single spot and elimination of reactant spots indicate termination. The product may be isolated by removal of solvents in vacuo.

Addition of amines such as

(III.)

and piperidines corresponding to

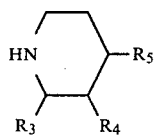

(V.)

may be used in equimolar amounts as a replacement for the 4-hydroxypiperidine in Example 3 to prepare other corresponding adducts of Formula Ib. Generally, the unsaturated compounds of Formula Ia. may be dissolved in dioxane, mixed with 5–25% molar excess of the amine, which may be previously dissolved in the same volume of water or dioxane, and allowed to stand at 20°–35° C. until addition is complete. Disappearance of the double bond, as measured by the change in infrared absorption or loss of the vinyl protons in the nuclear magnetic resonance spectrum, is used to monitor the progress of the reaction, as well as thin layer chromatography. The products may be isolated as described above and purified by fractional distillation under reduced pressure, crystallization in some cases, and by recrystallization of salts.

Following the procedures of Example 3, and substituting for the 1-[2-(n-propylsulfonyl)-2-propenyl]-4-piperidinol and 4-hydroxypiperidine, equimolar amounts of other reactants and substituted piperidines, there may be prepared additional novel compounds of the present invention, as shown in the following table:

| Reactant | Amine | Product |
|---|---|---|
| 1-[2-(n-(pentylsulfonyl)-2-prpopenyl]-4-piperidinol | dimethyl | 1-dimethylamino-3-(4-hydroxypiperidin-1-yl)-2-propyl n-pentyl sulfone |
| 1-[2-(n-undecylsulfonyl)-2-propenyl]-3,4-dimethylpiperidine | n-octyl | 1-n-octylamino-3-(3,4-dimethylpiperidin-1-yl)-2-propyl n-undecylsulfone |
| 1-[2-(n-propylsulfonyl)-2-propenyl]-3,4-dichloropiperidine | 3-methoxy piperidine | 1-(3-methoxypiperidin-1-yl)3(3,4-dichloropiperidin-1-yl)-2-propyl n-propylsulfone |
| 1-[2-phenylmethylsulfonyl)-2-propenyl]-2-ethyl-4-piperidinol | di-2-ethyl-hexyl | 1-di(2-ethylhexyl)amino-3-(2-ethyl-4-hydroxypiperidin-1-yl)-2-propyl phenylmethylsulfone |
| 1-[2-(1-naphthylsulfonyl)-2-propenyl]-2-fluoropiperidine | methyl n-octyl | 1-methyl n-octylamino-3-(2-fluoropiperidin-1-yl)-2-propyl 1-naphthylsulfone |
| 1-[2-(t-butylsulfonyl)-2-propenyl]-4-hydroxy-4-phenyl piperidine | di-n-propyl-amine | 1-di-n-propylamino-3-(4-hydroxy-4-phenyl-piperidin-1-yl)-2-propyl t-butylsulfone |

As already described above, the process of Example 1 (procedure A.) may be modified by increasing the molar ratio of amine:formaldehyde:sulfonylacetic acid from 1:2:1 to 2:2:1 in order to provide compounds of Formula Ic. Following this procedure, there may be prepared additional novel compounds of the present invention, as shown in the following table:

| Substituted Sulfonyl-acetic Acid | Substituted Piperdine | Product |
|---|---|---|
| n-hexyl | 4-hydroxy | 2-(n-hexylsulfonyl)-1,3-propanediylbis (4-hydroxy-piperidine) |
| n-dodecyl | 3-methoxy | 2-(n-dodecylsulfonyl)-1,2-propanediylbis(3-methoxy-piperidine) |
| n-dodecyl | 3,4-dimethyl | 2-(n-dodecylsulfonyl)-1,3-propanediylbis (3,4-dimethylpiperdine |
| n-octadecyl | 3-hydroxy-methyl | 2-(n-octadecylsulfonyl)-1,3-propanediylbis(3-hydroxymethylpiperidine) |
| phenylmethyl | 4-carboxamido | 2-(phenylmethylsulfonyl)-1,3-propanediylbis (4-carboxamidopiperidine) |
| 4-methoxy-phenyl | 3-carboethoxy | 2-(4-methoxyphenylsulfonyl)-1,3-propanediylbis(3-carboethoxypiperidine) |
| 1-naphthyl | 3-cyano | 2-(1-naphthylsulfonyl)-1,3-propanediylbis (3-cyano-piperidine) |
| furan-2-yl-methyl | 4-dimethyl-amino | 2-(furan-2-ylmethylsulfonyl)-1,3-propanediylbis(4-dimethylaminopiperidine) |
| 2-thenyl | 4-carbo-n-butoxy | 2(2-thenylsulfonyl)-1,3-propanediylbis (4-carbo-n-butoxy piperidine) |
| tetrahydro-furan-2-yl-methyl | 3-hydroxy | 2-(tetrahydrofuran-2-ylmethyl-sulfonyl)-1,3-propanediylbis (3-hydroxypiperidine) |

EXAMPLE 4

A mixture of 250 parts of 1-[2-(nn-propylsulfonyl)-2-propenyl]-4-piperidinol hydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen and mixed with 3.8 parts of magnesium stearate. They are then compressed into tablets suitable for oral administration.

The compound used in the foregoing example may be replaced by 25, 100, 250, or 500 parts of the piperidinol to produce tablets suitable for oral administration as an anti-inflammatory, antipyretic and/or analgesic according to the method of this invention.

EXAMPLE 5

A mixture of 50 parts of 1-[2-(phenylsulfonyl)-2-propenyl]-4-piperidinol pamoate, 3 parts of the calcium salt of lignin sulphonic acid, and 237 parts of water is ball-milled until the size of substantially all particles of the compound is less than 10 microns. The suspension is diluted with a solution containing 3 parts of the butyl ester of p-hydroxy-benzoic acid in 300 parts of water. There is thus obtained an aqueous suspension suitable for oral administration for therapeutic purposes.

EXAMPLE 6

A mixture of 250 parts of 2-(n-propylsulfonyl)-1,3-propanediylbis (4-hydroxypiperidine) succinate, 200 parts of maize starch and 30 parts of alginic acid is mixed with a sufficient quantity of a 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 7

A mixture of 500 parts 1-[2-(n-propylsulfonyl)-2-propenyl]-4-piperidinol hydrochloride, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 8

(1) Tablets—10,000 scored tablets for oral use, each containing 100 mg. of piperidinol, are prepared from the following ingredients.

1-[2-(phenylsulfonyl)-2-propenyl]-4-piperidinol adipate—1000
Starch, U.S.P.—350
Talc, U.S.P.—250
Calcium Stearate—35

The powdered adipate salt is granulated with a 4% w./v. aqueous solution of methylcellulose U.S.P. (1500 cps.). To the dried granules is added a mixture of the remainder of the ingredients and the final mixture compressed into tablets of proper weight.

(2) Capsules—10,000 two-piece hard gelatin capsules for oral use, each containing 50 mg. of the piperidinol adipate are prepared from the following ingredients:

| 1-[2-(phenylsulfonyl)-2-propenyl]-4-piperidinol adipate | 500 |
|---|---|
| Lactose, U.S.P. | 1000 |
| Starch, U.S.P. | 300 |
| Talc, U.S.P. | 65 |

*-continued*

| Calcium Stearate | 25 |
|---|---|

The powdered adipate salt is mixed with the starch-lactose mixture followed by the talc and calcium stearate. The final mixture is then encapsulated in the usual manner. Capsules containing 10 and 25 mg. of the adipate salt are also prepared by substituting 100 and 250 gm. for 500 gm. in the above formulation.

(3) Soft elastic capsules—One piece soft elastic capsules for oral use, each containing 50 mg. of 1-[2-(phenylsulfonyl)-2-propenyl]-4-piperidinol adipate are prepared in the usual manner by first dispersing the powdered active material in sufficient corn oil to render the material capsulatable.

(4) Aqueous suspension—An aqueous suspension for oral use containing in each 5 ml., 200 mg. of piperidinol is prepared from the following ingredients:

|  | GM |
|---|---|
| 1-[2-(phenylsulfonyl)-2-propenyl]-4-piperidinol | 400 |
| Methylparaben, U.S.P. | 7.5 |
| Propylparaben, U.S.P. | 2.5 |
| Saccharin sodium | 12.5 |
| Glycerin, 3000 ml. |  |
| Tragacanth Powder | 10 |
| Orange Oil Flavor | 10 |
| F.D. and C. Orange Dye | 7.5 |

What is claimed is:
1. A compound of the formula:

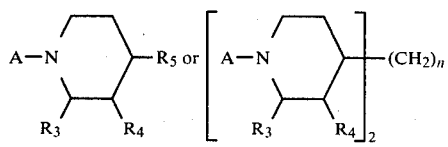

wherein A is

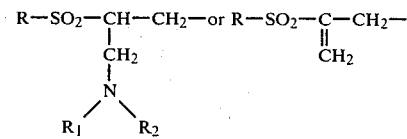

R is selected from the group consisting of $C_{3-18}$ alkyl; straight or branched chain; $C_{2-8}$ alkenyl; phenyl or naphthyl phenyl or naphthyl substituted with one or two members selected from the group consisting of halogen, $C_{1-4}$ alkyl, $C_{1-4}$ alkoxy, $C_{1-4}$ alkoxy $C_{1-4}$ alkyl, and nitro; phenylloweralkyl; phenylloweralkyl substituted with a member selected from the group consisting of halogen, $C_{1-4}$ alkyl, $C_{1-4}$ alkoxy, $C_{1-4}$ alkoxy $C_{1-4}$ alkyl, and nitro; and a heterocycle selected from the group consisting of imidazolyl, thienyl, thiazolyl, pyridyl, furyl, and tetrahydrofuran-2-yl;

$R_1$ and $R_2$ are independently selected from the group consisting of hydrogen; $C_{1-18}$ alkyl; $C_{2-8}$ alkenyl; hydroxy $C_{1-8}$ alkyl; and $C_{4-8}$ cycloalkyl; or $R_1$ and $R_2$ taken together with the nitrogen atom to which they are attached form a pyrrolidine or piperidine ring substituted at the 2-, 3-, 4-positions with $R_3$, $R_4$, and $R_5$, respectively;

$R_3$, $R_4$, and $R_5$ are selected from the group consisting of hydrogen; $C_{1-3}$ alkyl; $C_{2-3}$ alkenyl; halogen; hydroxy; hydroxy $C_{1-3}$ alkyl; phenyl; carboxyl; carboxamido; $C_{1-4}$ alkyl N-mono- and N,N-disubstitutedcarbonylamino; $C_{1-4}$ alkoxycarbonyl; 1-pyrrolidinyl; and 1-piperidinyl; and n is 0 to 3; and acid addition and quaternary salts thereof.

2. A compound according to claim 1 which is 1-[2-(n-propylsulfonyl)-2-propenyl]-4-piperidinol.

3. A compound according to claim 1 which is 1-[2-(phenylsulfonyl)-2-propenyl]-4-piperidinol.

4. A compound according to claim 1 which is 2-(n-propylsulfonyl)-1,3-propanediylbis(4-hydroxypiperidine).

5. A compound according to claim 1 which is 1-[2-(2-ethylhexylsulfonyl)-2-propenyl]-3-hydroxymethylpiperidine.

6. A compound according to claim 1 which is 1-[2-(3-pyridylsulfonyl)-2-propenyl]-2-methylpiperidine.

7. A compound according to claim 1 which is 2-(tetrahydrofuran-2-ylmethylsulfonyl)-1,3-propanediylbis-(3-hydroxypiperidine).

8. A compound according to claim 1 which is 1-dimethylamino-3-(4-hydroxypiperidin-1-yl)-2-propyl-n-pentylsulfone.

9. A method of treating a condition exhibiting at least one of the systems of pain, fever, and inflammation comprising administering to a patient in need of such a treatment a therapeutically effective amount of a compound of the formula:

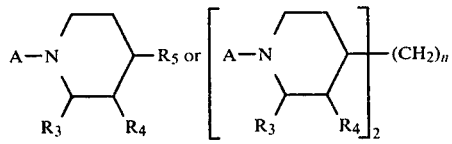

wherein

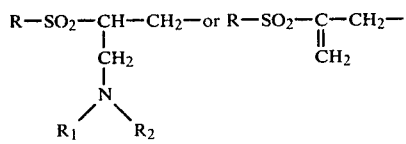

R is selected from the group consisting of $C_{3-18}$ alkyl; straight or branched chain; $C_{2-8}$ alkenyl; phenyl or naphthyl; phenyl or naphthyl substituted with one or two members selected from the group consisting of halogen, $C_{1-4}$ alkyl, $C_{1-4}$ alkoxy, $C_{1-4}$ alkoxy $C_{1-4}$ alkyl, and nitro; phenylloweralkyl; phenylloweralkyl substituted with a member selected from the group consisting of halogen, $C_{1-4}$ alkyl, $C_{1-4}$ alkoxy, $C_{1-4}$ alkoxy $C_{1-4}$ alkyl, and nitro; and a heterocycle selected from the group consisting of imidazolyl, thienyl, thiazolyl, pyridyl, furyl, and tetrahydrofuran-2-yl;

$R_1$ and $R_2$ are independently selected from the group consisting of hydrogen; $C_{1-18}$ alkyl; $C_{2-8}$ alkenyl; hydroxy $C_{1-8}$ alkyl; and $C_{4-8}$ cycloalkyl; or $R_1$ and $R_2$ taken together with the nitrogen atom to which they are attached form a pyrrolidine or piperidine ring substituted at the 2-, 3-, 4-positions with $R_3$, $R_4$, and $R_5$, respectively;

$R_3$, $R_4$, and $R_5$ are selected from the group consisting of hydrogen; $C_{1-3}$ alkyl; $C_{2-3}$ alkenyl; halogen; hydroxy; hydroxy $C_{1-3}$ alkyl; phenyl; carboxyl; carboxamido; $C_{1-4}$ alkyl N-mono- and N,N-disubstitutedcarbonylamino; $C_{1-4}$ alkoxycarbonyl; 1-pyrrolidinyl; and 1-piperidinyl; and n is 0 to 3;

and acid addition and quaternary salts thereof.

10. A pharmaceutical composition for treating a condition exhibiting at least one of the symptoms of pain, fever, and inflammation, comprising a pharmaceutically acceptable, non-toxic carrier, and a therapeutically effective amount of a compound of the formula:

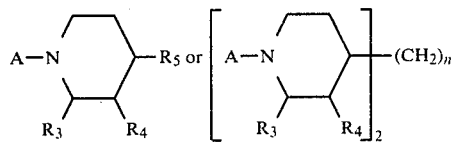

wherein

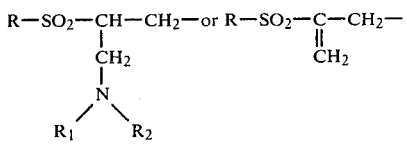

R is selected from the group consisting of $C_{3-18}$ alkyl; straight or branched chain; $C_{2-8}$ alkenyl; phenyl or naphthyl; phenyl or naphthyl substituted with one or two members selected from the group consisting of halogen, $C_{1-4}$ alkyl, $C_{1-4}$ alkoxy, $C_{1-4}$ alkoxy $C_{1-4}$ alkyl, and nitro; phenylloweralkyl; phenylloweralkyl substituted with a member selected from the group consisting of halogen, $C_{1-4}$ alkyl, $C_{1-4}$ alkoxy, $C_{1-4}$ alkoxy $C_{1-4}$ alkyl, and nitro; and a heterocycle selected from the group consisting of imidazolyl, thienyl, thiazolyl, pyridyl, furyl, and tetrahydrofuran-2-yl;

$R_1$ and $R_2$ are independently selected from the group consisting of hydrogen; $C_{1-18}$ alkyl; $C_{2-8}$ alkenyl; hydroxy $C_{1-8}$ alkyl; and $C_{4-8}$ cycloalkyl; or $R_1$ and $R_2$ taken together with the nitrogen atom to which they are attached form a pyrrolidine or piperidine ring substituted at the 2-, 3-, 4-positions with $R_3$, $R_4$, and $R_5$, respectively;

$R_3$, $R_4$, and $R_5$ are selected from the group consisting of hydrogen; $C_{1-3}$ alkyl; $C_{2-3}$ alkenyl; halogen; hydroxy; hydroxy $C_{1-3}$ alkyl; phenyl; carboxyl; carboxamido; $C_{1-4}$ alkyl N-mono- and N,N-disubstitutedcarbonylamino; $C_{1-4}$ alkoxycarbonyl; 1-pyrrolidinyl; and 1-piperidinyl; and n is 0 to 3;

and acid addition and quaternary salts thereof.

11. A composition according to claim 10 wherein the compound is 1-[2-(n-propylsulfonyl)-2-propenyl]-4-piperidinol.

12. A composition according to claim 10 wherein the compound is 1-[2-(phenylsulfonyl)-2-propenyl]-4-piperidinol.

13. A composition according to claim 10 wherein the compound is 2-(n-propylsulfonyl)-1,3-propanediylbis(4-hydroxypiperidine).

14. An antimicrobial composition comprising an inert solid carrier and an antimicrobially effective amount of a compound of the formula:

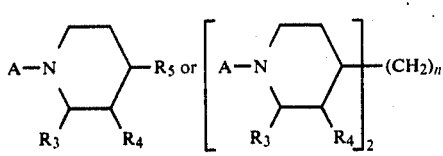

wherein A is

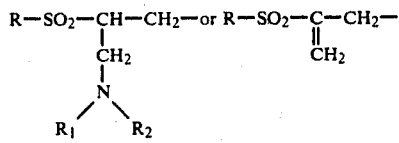

R is selected from the group consisting of $C_{3-18}$ alkyl; straight or branched chain; $C_{2-8}$ alkenyl; phenyl or naphthyl; phenyl or naphthyl substituted with one or two members selected from the group consisting of halogen, $C_{1-4}$ alkyl, $C_{1-4}$ alkoxy, $C_{1-4}$ alkoxy $C_{1-4}$ alkyl, and nitro; phenylloweralkyl; phenylloweralkyl substituted with a member selected from the group consisting of halogen, $C_{1-4}$ alkyl, $C_{1-4}$ alkoxy, $C_{1-4}$ alkoxy $C_{1-4}$ alkyl, and nitro; and a heterocycle selected from the group consisting of imidazolyl, thienyl, thiazolyl, and pyridyl, furyl, and tetrahydrofuran-2-yl;

$R_1$ and $R_2$ are independently selected from the group consisting of hydrogen; $C_{1-18}$ alkyl; $C_{2-8}$ alkenyl; hydroxy $C_{1-8}$ alkyl; and $C_{4-8}$ cycloalkyl; or $R_1$ and $R_2$ taken together with the nitrogen atom to which they are attached form a pyrroldine or piperidine ring substituted at the 2-, 3-, 4-positions with $R_3$, $R_4$, and $R_5$, respectively;

$R_3$, $R_4$, and $R_5$ are selected from the group consisting of hydrogen; $C_{1-3}$ alkyl; $C_{2-3}$ alkenyl; halogen; hydroxy; hydroxy $C_{1-3}$ alkyl; phenyl; carboxyl; carboxamido; $C_{1-4}$ alkyl N-mono- and N,N-disubstitutedcarbonylamino; $C_{1-4}$ alkoxycarbonyl; 1-pyrrolidinyl; and 1-piperidinyl; and n is 0 to 3;

and acid addition and quaternary salts thereof.

15. A composition according to claim 14 wherein the carrier is selected from the group consisting of talc, corn starch, alumina and diatomaceous earth.

16. A composition according to claim 14 wherein the compound is 1-[2-(n-propylsulfonyl)-2-propenyl]-4-piperidinol.

17. A composition according to claim 14 wherein the compound is 1-[2-(phenylsulfonyl)-2-propenyl]-4-piperidinol.

18. A composition according to claim 14 wherein the compound is 2-(-propylsulfonyl)-1,3-propanediylbis(4-hydroxypiperidine).

* * * * *